United States Patent [19]

Webb et al.

[11] 4,226,934

[45] Oct. 7, 1980

[54] LIGHT SENSITIVE PHOTOGRAPHIC MATERIAL CONTAINING DEVELOPMENT INHIBITOR RELEASING COMPOUNDS

[75] Inventors: Terence C. Webb, Witham; David L. R. Reeves, Brentwood, both of England

[73] Assignee: Ciba-Geigy AG, Basel, Switzerland

[21] Appl. No.: 928,211

[22] Filed: Jul. 26, 1978

[30] Foreign Application Priority Data

Aug. 12, 1977 [GB] United Kingdom ............... 33883/77

[51] Int. Cl.$^2$ ............................................. G03C 5/30
[52] U.S. Cl. .................................. 430/443; 430/382; 430/445; 430/446; 430/448; 430/505; 430/544; 430/957
[58] Field of Search .................. 96/95, 66.3; 430/446, 430/448, 505, 957, 443

[56] References Cited

U.S. PATENT DOCUMENTS

| | | | |
|---|---|---|---|
| 3,632,345 | 1/1972 | Marx et al. ........................... | 96/95 |
| 3,632,373 | 1/1972 | O'Connell et al. .................. | 96/22 |
| 3,856,588 | 12/1974 | Hashimoto et al. ................ | 148/188 |
| 3,890,169 | 6/1975 | Schwartz ............................. | 148/187 |
| 3,928,041 | 12/1975 | Fujiwhara et al. ................. | 96/66.3 |
| 4,055,443 | 10/1977 | Stepanovich et al. ............. | 148/187 |
| 4,058,413 | 11/1977 | Welch et al. ........................ | 148/187 |
| 4,075,021 | 2/1978 | Kikuchi et al. ..................... | 96/95 |
| 4,116,722 | 9/1978 | Kamei et al. ....................... | 148/187 |
| 4,121,934 | 10/1978 | Yagihara et al. ................... | 96/95 |

OTHER PUBLICATIONS

Ishii et al., "Influence . . . on Gallium Arsenide", *J. Org. Electrochemical Society*, vol. 124, No. 11, (11/77), pp. 1784-1794.

Hunsperger, "Ion–Implanted . . . in GaAs", *Solid–State Electronics*, vol. 18, pp. 349-353, (1975).

*Primary Examiner*—J. Travis Brown
*Attorney, Agent, or Firm*—Sprung, Felfe, Horn, Lynch & Kramer

[57] ABSTRACT

A light-sensitive photographic material is provided which comprises, coated on a photobase, at least one silver halide emulsion layer, said emulsion layer or a layer adjacent thereto containing a development inhibitor releasing compound of the formula

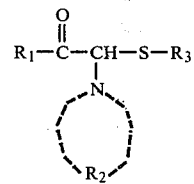

wherein $R_1$ is substituted phenyl which contains a ballasting alkyl group, $R_2$ represents the atoms necessary to complete a five or six membered heterocyclic ring system which may be further substituted and $R_3$ is an aryl or heterocyclic radical, any of which ring systems may be further substituted, the group —S—$R_3$ being a development inhibiting group.

10 Claims, No Drawings

LIGHT SENSITIVE PHOTOGRAPHIC MATERIAL CONTAINING DEVELOPMENT INHIBITOR RELEASING COMPOUNDS

This invention relates to photographic material with improved properties which contains compounds that react with the oxidation products of developing agents to release substances that inhibit development (DIR-compounds or couplers).

The use of compounds which release development inhibitor compounds imagewise is well known in the photographic art to produce useful inter-layer and intra-layer effects. Such compounds and their use in the photographic field are disclosed, for example in U.S. Pat. Nos. 3,227,554, 3,632,345, 3,928,041 and 4,049,455.

While various development inhibitor releasing compounds have been produced hitherto the majority of these compounds are not completely satisfactory. For example in the case of a development inhibitor releasing compound which forms a dye upon colour development, the colour coupler residue of the DIR-compound must be carefully selected to achieve the correct colour balance in the photographic colour image because of the specific absorption properties required of the resulting dye. It has proved difficult to produce useful DIR-colour couplers.

On the other hand those development inhibitor releasing compounds which form no dye with the oxidation products of a colour development agent either possess extremely low reactivity or cause serious speed losses during development.

However the compounds of the present invention form colourless compounds when reacted with the oxidation products of the colour developing agent. The colourless residue does not constitute any part of the resulting image. This has the advantage that the novel releasing compounds can be applied to any required layer in the photographic material. Furthermore, the compounds of the present invention have an extremely high reactivity with the oxidation products of the colour developing agent. Consequently only small quantities of compound are required to produce excellent intra-image and inter-image effects without serious speed losses.

An object of this invention is to provide new development inhibitor releasing compounds having high intra-image and inter-image effects without serious speed losses and an excellent reactivity with the oxidation products of the colour developing agent.

The novel DIR-couplers are of the formula

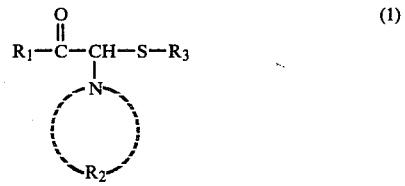

wherein $R_1$ is substituted phenyl which contains a ballasting alkyl group, $R_2$ represents the atoms necessary to complete a five or six membered heterocyclic ring system which may be further substituted and $R_3$ is an aryl, or heterocyclic radical, any of which ring systems may be further substituted, the group $—S—R_3$ being a development inhibiting group.

According to another aspect of the present invention there is provided a light-sensitive photographic material which comprises, coated on a photobase, at least one silver halide emulsion layer, the said emulsion layer or a layer adjacent thereto containing a compound of the general formula (1).

Preferably the compound of formula (1) is present in the silver halide emulsion layer.

A further object of the present invention is to provide a process for the production of a photographic image which comprises imagewise exposing a light-sensitive photographic silver halide material which comprises in at least one silver halide layer or a layer adjacent thereto novel DIR-couplers and developing the exposed silver halide with a paraphenylene diamine colour developing agent thereby to liberate imagewise the group $R_3—S^\ominus$.

By ballasting alkyl group is meant a straight or branched chain alkyl group, optionally substituted, having at least 10 carbon atoms. (The alkyl group and its substituents contain at least 10 carbon atoms). The presence of the ballasting alkyl group in the DIR compound renders this compound substantive to the layer in which it is coated.

In the compounds of formula (1) both the group

and the group

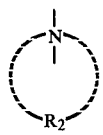

which are attached to the central methine group fo the compound are electron withdrawing groups. This means that the methine group is an activated methine group which can couple with oxidised colour developers of the para-phenylene diamine type in the same way as colour couplers couple with such oxidised colour developers. The coupling of the compound of formula (1) with oxidised colour developer leads to an unstable compound in which elimination occurs and the group $R_3—S^\ominus$ is released. The compound $HS-R_3$ is a development inhibitor compound.

Suitable $R_3—S—$ groups are members of the mercapto pyrimidine series, members of the mercapto thiadiazole series such as a 2-mercapto thiadiazolotriazine, members of the mercapto triazine series, members of the mercapto tetrazole series, or members of the mercapto triazole series, or an optionally substituted mercapto benzene, of which the substituents may be for example carboxyl, nitro or acylated amino groups, such as 1-mercapto-2-benzoic acid, 1-mercapto-2-nitrobenzene, or 1-mercapto-3-heptadecanoylamino benzene.

$R_3$ is thus optionally substituted pyrimidyl, thiadiazolyl, triazinyl, tetrazolyl, triazolyl, pyridyl (substituents $C_1-C_4$ alkyl and/or hydroxyl), phenyl (substituents carboxyl, nitro or acylated amino groups, wherein acyl contains 1 to 18 carbon atoms) or benzthiazolyl.

Preferably $R_3$ is a phenyl substituted tetrazole group.

Preferably $R_2$ represents the atoms necessary to complete an optionally substituted triazole, tetrazole, pyrazole or imidazole ring system. Examples of substituents which may be present in the ring system are alkyl groups ($C_1$-$C_4$), alkylthio groups (R—S—, $C_1$-$C_8$) and phenyl or halogenphenyl (chlorophenyl) groups.

Particularly useful groups $R_1$ are those of the formula

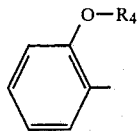
(2)

where $R_4$ is a ballasting alkyl group or contains a ballasting optionally substituted alkyl group of at least 10 carbon atoms.

Other useful groups $R_1$ are those of the formula

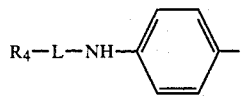
(3)

where L is an —$SO_2$- or —CO-link and $R_4$ is as just defined.

Preferred are those DIR compounds of formula (1) wherein $R_1$ is a group of the formula

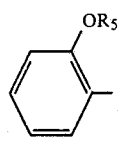
(4)

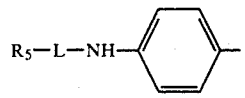
(5)

or

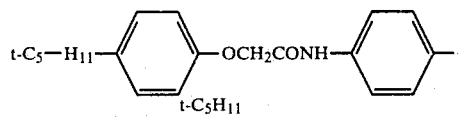
(6)

wherein L is —$SO_2$— or —CO— and $R_5$ is alkyl of 10 to 18 carbon atoms, $R_2$ represents the atoms necessary to complete an optionally alkyl of 1 to 4 carbon atoms or alkylthio of 1 to 8 carbon atoms substituted tetrazole, triazole, pyrazole or imidazole ring system and $R_3$ is pyrimidyl, thiadiazolyl, triazinyl, tetrazolyl or triazolyl, pyridyl, optionally substituted by alkyl of 1 to 4 carbon atoms or hydroxyl or phenyl optionally substituted by carboxyl, nitro or acylamino wherein acyl contains 1 to 18 carbon atoms, or benzthiazolyl.

Compounds of formula (1) may be prepared by reacting a solution of a compound of the general formula

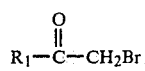
(7)

with a solution of a compound of formula

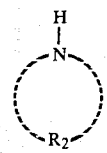
(8)

where $R_1$ and $R_2$ have the meanings assigned to them above in the presence of a base, reacting a solution of the resultant compound of the formula

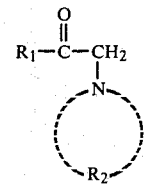
(9)

with halogen to form a compound of the formula

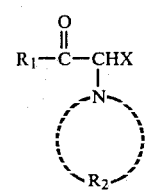
(10)

where X is halogen and reacting the solution of a compound of formula (10) with a compound of the formula M—S—$R_3$ where $R_3$ has the meaning assigned to it above and M is an alkali metal.

Preferably in steps 1 and 3 of the above process the solvent is acetonitrile.

Preferably the base used in the first step is triethylamine. Preferably the halogen used in the second step is bromine. Preferably M is potassium.

The DIR compounds of the present invention may be used in any photographic product which can be processed by chromogenic process and in which increased image sharpness and/or interlayer effects are desired. Thus the greatest use of the DIR compounds of the present invention is expected to be in the field of colour photographic material and in particular in colour negative film material. When used in colour film material it is expected that the DIR compounds of the present invention will be present in colour-sensitised silver halide emulsion layers which comprise at least one colour coupler. Useful amounts of DIR compounds present in such silver halide emulsion layers are 5 to 10 mole % of the colour coupler present.

Examples of specific compounds according to the present invention which release a development inhibitor compound on coupling are thos of the following formulae:

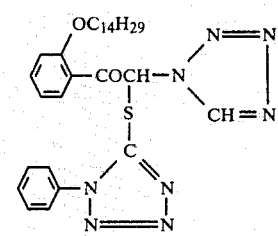
(101)

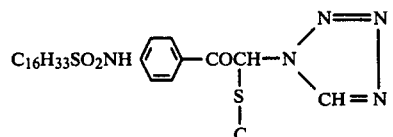 (102)

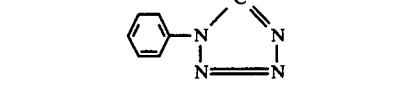 (103)

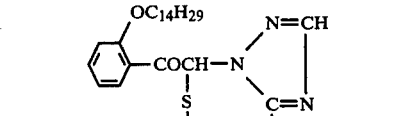 (104)

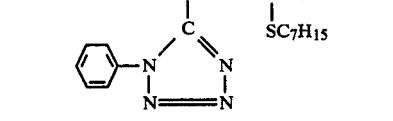 (105)

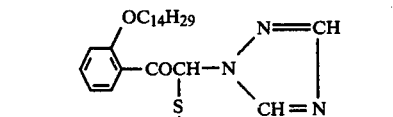 (106)

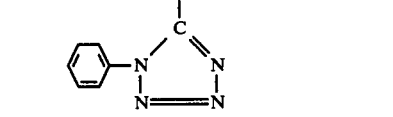 (107)

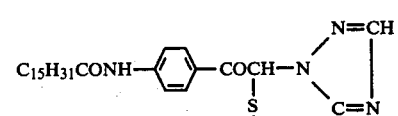 (108)

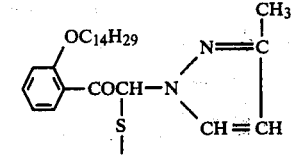 (109)

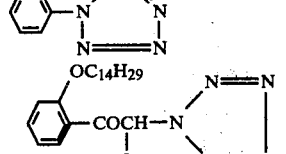 (110)

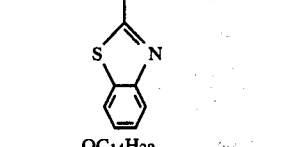 (111)

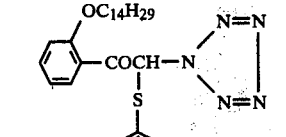 (112)

The following Examples will serve to illustrate the invention:

EXAMPLE 1

Preparation of compound of formula (101)

(a) α-(Tetrazolyl)-o-tetradecyloxyacetophenone

To a solution of 14.6 g of o-tetradecyloxyphenacyl-bromide in 75 ml of acetonitrile was added a solution of 2.8 g of tetrazole and 4.0 g of triethylamine in 75 ml of acetonitrile. The reaction mixture was stirred at reflux temperature for 2 hours then evaporated to dryness. The residue was dissolved in chloroform and the organic layer washed with water, dried over magnesium-sulfate, filtered and evaporated to give the crude compound. Recrystallisation from petrol (b.p. 60°–80° C.) gave the acetophenone derivative as a fine white powder. Yield: 12.7 g; m.p. 67° to 69° C.

(b)
α-Bromo-α-tetrazolyl-o-tetradecyloxyacetophenone

To 10.8 g of the above acetophenone derivative in 150 ml of chloroform maintained at 50° C. was added dropwise a solution of 4.5 g of bromine (1.5 ml) in 50 ml of chloroform. The reaction mixture was stirred for a further hour at 50° C. and then evaporated. The residue was recrystallised from petrol (b.p. 60°–80° C.) to afford the bromo derivative as a fine white powder. Yield: 10.5 g; m.p. 39° to 41° C.

(c)
α-Tetrazolyl-α-[1-phenyltetrazole-5-thiyl-]-o-tetradecyloxyacetophenone A mixture of 6.0 g of the bromo derivative and 2.75 g of the potassium salt of 1-phenyl-5-thiotetrazole in 45 ml of acetonitrile was stirred at reflux temperature for 2 hours. The reaction mixture was cooled, filtered and evaporated. The residue was recrystallised from methanol to give the compound of formula (101) as a white powder.

Yield: 5.1 g; m.p. 60° to 61° C. $C_{30}H_{40}N_8O_2S$ Found: C 62.44; H 7.07; N 19.17% Calculated: C 62.47; H 6.98; N 19.42%

The compound of the formula (102) may be prepared in a similar manner.

EXAMPLE 2
Preparation of the compound of formula (103)

(a)
α-3(5)-Heptylthiotriazole-o-tetradecyloxyacetophenone

To a solution of 10 g of o-tetradecyloxyphenacyl bromide in 30 ml of warm acetonitrile was added to a solution of 6 g of 3(5)-heptylthiotriazole and 3 g of triethylamine in 20 ml of acetonitrile. The reaction mixture was stirred at room temperature for 6 hours and then evaporated. The residue was dissolved in 50 ml of ethyl acetate and the organic layer washed twice with 50 ml water, dried over magnesium sulfate, filtered and evaporated. Recrystallisation of the residue from methanol gave the acetophenone derivative as an off-white powder. Yield: 7.8 g; m.p. 61° to 62° C.

(b)
α-Bromo-α-[3(5)-heptylthiotriazole]-o-tetradecyloxyacetophenone

To a stirred solution of 5.1 g of the above derivative in 75 ml of chloroform at 60° C. was added over a period of 2 hours a solution of 1.6 g of bromine in 10 ml of chloroform. The reaction mixture was stirred at reflux temperature for a further 2 hours and then evaporated. Trituration of the residual oil in methanol at 0° C. afforded the product in solid form. Subsequent filtration gave the α-bromo derivative as an off-white powder. Yield: 5.4 g; m.p. 45° to 46° C.

(c)
α-[3(5)-Heptylthiotriazole]-α-[1-phenyltetrazole-5-thiyl]-o-tetradecyloxyacetophenone 5.0 g of the bromo-derivative and 1.8 g of the potassium salt of 1-phenyl-5-thiotetrazole were stirred in 35 ml acetonitrile at gentle reflux for 2 hours. The reaction mixture was cooled to room temperature, filtered and evaporated. Recrystallisation of the residue from methanol gave the compound of formula (103) as a pure white powder.

Yield: 4.1 g; m.p. 68° to 70° C. $C_{38}H_{55}N_7O_2S_2$ Found: C 64.67; H 7.1; N 13.91% Calculated: C 64.74; H 7.72; N 13.91%

The compound of formula (104) may be prepared in a similar manner.

EXAMPLE 3
Preparation of the compound of formula (105)

(a)
α-[3(5)-Heptylthiotriazole]-p-hexadecylamidoacetophenone

A mixture of 11.7 g of p-hexadecylamidophenacyl bromide and 6.0 g of the potassium salt of 3(5)-heptylthiotriazole was stirred in 30 ml of acetonitrile at reflux temperature for 2½ hours. The reaction mixture was cooled, filtered and evaporated. The residue was recrystallised from methanol to give a fine white solid. Yield: 12.4 g; m.p. 110° to 112° C.

(b)
α-Bromo-α[3(5)-heptylthiotriazole]-p-hexadecylamidoacetophenone

To 8.0 g of the acetophenone derivative in 100 ml of chloroform was added a solution of 2.4 g of bromine (0.8 ml) in 50 ml of chloroform. The reaction mixture was stirred at room temperature for 4 hours and evaporated to give the α-bromo-derivative as a colourless viscous oil. Yield: 9.0 g.

(c)
α-[3(5)-Heptylthiotriazole]-α-[phenyltetrazole-5-thiyl-]-p-hexadecylamidoacetophenone 4.4 g of the bromo-derivative and 1.6 g of the potassium salt of 1-phenyl-5-thiotetrazole were stirred in 50 ml of acetonitrile at reflux temperature for 1 hour. The reaction mixture was cooled, filtered and evaporated. The product was purified by column chromatography on silica gel to give the compound of formula (105) as a waxy solid.

Yield: 3.4 g. $C_{40}H_{58}N_8O_2S_2$ Found: C 64.66; H 8.17; N 14.77%. Calculated: C 64.36; H 7.83; N 15.00%.

Compounds of the formulae (106) to (109) may be prepared in a similar manner.

EXAMPLE 4
Preparation of the compound of formula (110)

α-[2-Mercaptobenzthiazole]-α-[Tetrazolyl]-o-tetradecyloxyacetophenone

A solution of 4.79 g of α-bromo-α-tetrazoyl-o-tetradecyloxyacetophenone and 2.1 g of the potassium salt of 2-mercaptobenzthiazole in 50 ml of acetonitrile was stirred at reflux for 10 hours. The reaction mixture was evaporated, the residue dissolved in 50 ml of ethyl acetate and the organic layer washed three times with 50 ml of water, dried over sodium sulfate, filtered and evaporated. Chromatography on silica gel and recrystallisation from methanol gave a light yellow powder. Yield: 3.1 g; m.p. 49° to 50° C. $C_{30}H_{39}N_5O_2S_2$ Found: C 63.61; H 6.84; N 12.48%. Calculated: C 63.72; H 6.90; N 12.39%.

EXAMPLE 5
Preparation of the compound of formula (111)

α-[4-Nitrophenylthio]-α-[tetrazoyl]-o-tetradecyloxyacetophenone

A solution of 4.79 g of α-bromo-α-tetrazoyl-o-tetradecyloxyacetophenone and 2.0 g of the potassium salt of 4-nitrothiophenol in 50 ml of acetonitrile was stirred at reflux for 2 hours. The reaction mixture was evaporated and the residue dissolved in chloroform, washed three times with 50 ml of water, dried over sodiumsulfate, filtered and evaporated. Chromatography on silica gel and recrystallisation from methanol gave the compound of formula (111) as a light yellow powder. Yield: 2.1 g; m.p. 52° to 53° C. $C_{29}H_{39}N_5O_4S$ Found: C 63.05; H 7.09; N 12.49% Calculated: C 62.93; H 7.05; N 12.66%.

EXAMPLE 6

Use example-development inhibition 10 g of 1-(2,4,6-Trichlorophenyl)-3-(3-[2,4-ditertamylphenoxy)acetamido]benzamido)-5-pyrazolone were dissolved in a solution of 10 g of tricresylphosphate and 10 g of ethyl acetate. A solution of 80 g of gelatin was added followed by 20 ml of water and 20 ml of an aqueous solution (10%) of the sodium salt of an alkylnaphthalene sulfonic acid (wetting agent). The whole was then dispersed using an ultrasonic mixer.

24 g of the coupler emulsion were added to 40 g of a silver iodo-bromide emulsion having a silver content of 4.9 g and an average iodide content of 8.8 molar percent.

48 g of a gelatin solution and 38 ml of the wetting agent solution mentioned before were added and the whole made up to 200 g with water.

The mixture was coated onto subbed triacetate film base to give a silver coating weight of 20 mg per $dm^2$ and a coupler coating weight of 6.4 mg per $dm^2$. Above this was coated a 20 mg per $dm^2$ gelatin layer containing a triazine hardener.

The coating was exposed to a continuous wedge and then subjected to the following processing sequence at 37.8° C.

| | |
|---|---|
| 1. Colour development | 3.25 mins |
| 2. Bleach | 6.50 mins |
| 3. Wash | 3.25 mins |
| 4. Fix | 6.50 mins |
| 5. Wash | 3.25 mins |
| 6. Stabilize | 1.50 mins. |

The processing baths had the following compositions:

| 1. Developer | |
|---|---|
| Potassium carbonate | 37.5 g |
| Sodium metabisulphite (anhydrous) | 4.25 g |
| Potassium iodide | 2.0 mg |
| Sodium bromide | 1.3 g |
| Hydroxylamine sulphate | 2.0 g |
| 4-(N-ethyl-N-β-hydroxyethylamino)-2-methylaniline sulphate | 4.75 g |
| Water to | 1 liter |

| 2. Bleach | |
|---|---|
| Ammonium bromide | 150 g |
| Ferric ammonium ethylenediamine tetracetate | 175 ml |
| Glacial acetic acid | 10,5 ml |
| Sodium nitrate | 35 g |
| Water to | 1 liter |

| 4. Fix | |
|---|---|
| Ammonium thiosulphate (50%) | 162 ml |
| Diethylene triamine penta-acetic acid | 1.25 g |
| Sodium metabisulphite (anhydrous) | 12,4 g |
| Sodium hydroxide | 2.4 g |
| Water to | 1 liter |

| 6. Stabiliser | |
|---|---|
| 35% formaldehyde solution | 5.0 ml |
| Water to | 1 liter |

The above procedure (CONTROL) produced the following photographic results for maximum contrast (γm) and contrast adjusted speed (δγ/4):

| Control | γm | γ/4 (log E units) |
|---|---|---|
| Pyrazolone coupler alone | 1.19 | 2.74 |

To allow for the effect of contrast on foot speed the δγ/4 value has been quoted. This is defined as:
δγ/4=(Speed at a density level of fog)+γ/4

The above coating procedure was then repeated but in addition to the pyrazolone coupler, coatings were made which individually incorporated 5, 10 or 20 mole percent of the DIR compounds, and the percentage γm suppression and change in δγ/4 compared with the control were measured.

TABLE 1

| DIR Compound | %γm Suppression | Change in αγ/4 |
|---|---|---|
| 5% Level of Compound (101) | 59 | +0.15 |
| 10% Level of Compound (101) | 72 | +0.14 |
| 5% Level of Compound (103) | 37 | +0.08 |
| 10% Level of Compound (103) | 52 | +0.12 |
| 5% Level of Compound (104) | 71 | +0.15 |
| 10% Level of Compound (104) | 82 | +0.18 |
| 10% Level of Compound A | 6 | −0.20 |
| 20% Level of Compound A (Comparison) | 17 | −0.21 |
| 5% Level of Compound B | 32 | −0.09 |
| 10% Level of Compound B (Comparison) | 42 | −0.13 |

The DIR compound A has the following structure:

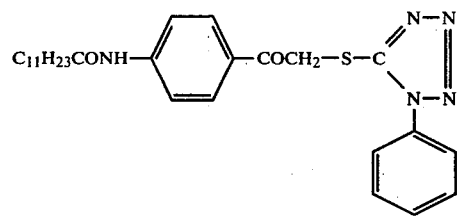

and is of the type disclosed in U.S. Pat. No. 3,632,345.
The DIR compound B has the following structure:

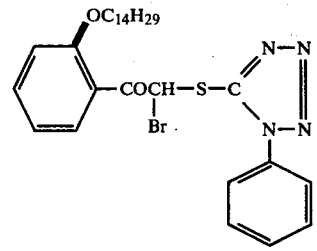

and is of the type disclosed in U.S. Pat. No. 3,928,041.
Table 1 clearly shows that the compounds of the present invention are significantly more active (i.e. they exhibit greater development inhibition) as shown by the high γ max suppression values compared with those of the known DIR compounds A and B.

Furthermore the DIR compounds of the current case show no speed loss as shown by the positive δγ/4 values, compared with the known DIR compounds A and B.

What we claim is:

1. A light-sensitive photographic material which comprises, coated on a photobase, at least one silver halide emulsion layer, said emulsion layer or a layer adjacent
thereto containing a development inhibitor releasing compound of the formula

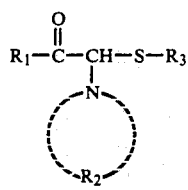

wherein $R_1$ is a group of the formulae

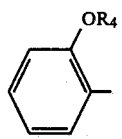

or

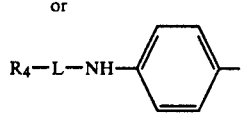

wherein L is $-SO_2-$ or $-CO-$ and $R_4$ is a ballasting alkyl group or contains an unsubstituted or substituted ballasting alkyl group of at least 10 carbon atoms, $R_2$ represents the atoms necessary to complete a tetrazole, triazole, pyrazole or imidazole ring system which is unsubstituted or substituted by alkyl or alkylthio and $R_3$ is unsubstituted or substituted pyrimidyl, thiadiazolyl, triazinyl, tetrazolyl, triazolyl, pyridyl, phenyl or benzthiazolyl the groups $-S-R_3$ being the development inhibiting group.

2. A light sensitive material according to claim 1, wherein $R_3$ is pyrimidyl, thiadiazolyl, triazinyl, triazolyl, tetrazolyl or phenyl which is unsubstituted or substituted by carboxyl, nitro or $C_1-C_{18}$-acylamino.

3. A light sensitive photographic material according to claim 1, wheerein $R_1$ is a group of the formulae

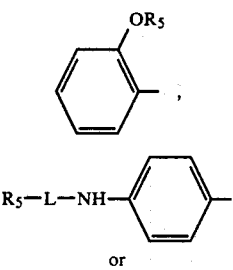

or

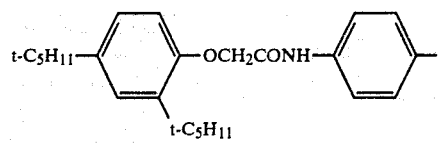

wherein L is $-SO_2-$ or $-CO-$ and $R_5$ is alkyl of 10 to 18 carbon atoms, $R_2$ represents the atoms necessary to complete an optionally alkyl of 1 to 4 carbon atoms or alkylthio of 1 to 8 carbon atoms substituted tetrazole, triazole, pyrazole or imidazole ring system and $R_3$ is pyrimidyl, thiadiazolyl, triazinyl, tetrazolyl or triazolyl, pyridyl optionally substituted by alkyl of 1 to 4 carbon atoms or hydroxyl or phenyl optionally substituted by carboxyl, nitro or acylamino, wherein acyl contains 1 to 18 carbon atoms, or benzthiazolyl.

4. A light sensitive photographic material according to claim 3, wherein $R_3$ is a phenyl substituted tetrazole group.

5. A light-sensitive photographic material according to claim 1 wherein the DIR compound is present in the silver halide emulsion layer.

6. A process for the production of a photographic image which comprises imagewise exposing a light-sensitive photographic silver halide material which contains in at least one silver halide layer or a layer adjacent thereto a compound of formula

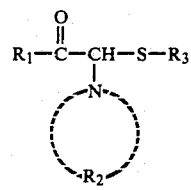

wherein $R_1$, $R_2$ and $R_3$ have the meanings indicated in claim 1 and developing the exposed silver halide with a paraphenylene diamine colour developing agent thereby to liberate imagewise the group $R_3-S^\ominus$.

7. A process according to claim 6, wherein $R_1$ is a group of the formulae

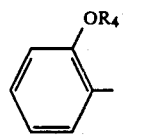

or

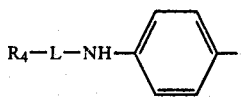

wherein L is $-SO_2-$ or $-CO-$ and $R_4$ is a ballasting alkyl group or contains an optionally substituted ballasting alkyl group of at least 10 carbon atoms, $R_2$ represents the atoms necessary to complete a tetrazole, triazole, pyrazole or imidazole ring system optionally substituted by alkyl or alkylthio, and $R_3$ is optionally substituted pyrimidyl, thiadiazolyl, triazinyl, tetrazolyl, triazolyl, pyridyl, phenyl or benzthiazolyl.

8. A process according to claim 7, wherein $R_3$ is pyrimidyl, thiadiazolyl, triazinyl, triazolyl, tetrazolyl or an optionally substituted phenyl.

9. A process according to claim 7, wherein $R_1$ is a group of the formula

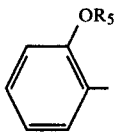

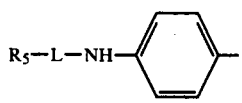

or

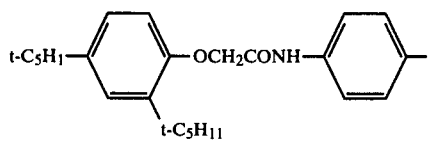

wherein L is $-SO_2-$ or $-CO-$ and $R_5$ is alkyl of 10 to 18 carbon atoms, $R_2$ represents the atoms necessary to complete an optionally alkyl of 1 to 4 carbon atoms or alkylthio of 1 to 8 carbon atoms substituted tetrazole, triazole, pyrazole or imidazole ring system and $R_3$ is pyrimidyl, thiadiazolyl, triazinyl, tetrazolyl or triazolyl, pyridyl optionally substituted by alkyl of 1 to 4 carbon atoms or hydroxyl, or phenyl optionally substituted by carboxyl, nitro or acylamino, wherein acyl contains to 18 carbon atoms, or benzthiazolyl.

10. A process according to claim 9, wherein $R_3$ is a phenyl substituted tetrazole group.

* * * * *